United States Patent [19]

Hamprecht et al.

[11] 4,426,219
[45] Jan. 17, 1984

[54] 2H-1,2,4,6-THIATRIAZINE-1-DIOXIDES AND THEIR USE FOR CONTROLLING UNDESIRABLE PLANT GROWTH

[75] Inventors: Berhard Hamprecht, Weinheim; Bruno Wuerzer, Otterstadt, both of Fed. Rep. of Germany

[73] Assignee: BASF Aktiengesellschaft, Fed. Rep. of Germany

[21] Appl. No.: 410,836

[22] Filed: Aug. 23, 1982

[30] Foreign Application Priority Data

Aug. 28, 1981 [DE] Fed. Rep. of Germany ....... 3134143

[51] Int. Cl.³ .................... C07D 285/00; A01N 43/72
[52] U.S. Cl. ........................................... 71/91; 544/7
[58] Field of Search ................................ 71/91; 544/7

[56] References Cited

U.S. PATENT DOCUMENTS

| 4,013,447 | 3/1977 | Kay | 71/91 |
| 4,316,014 | 2/1982 | Hamprecht et al. | 544/7 |
| 4,316,015 | 2/1982 | Hamprecht et al. | 544/7 |

FOREIGN PATENT DOCUMENTS 1946262 3/1971 Fed. Rep. of Germany .

Primary Examiner—John M. Ford
Attorney, Agent, or Firm—Keil & Witherspoon

[57] ABSTRACT

2H-1,2,4,6-thiatriazine-1,1-dioxides of the formula I

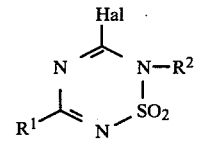

where $R^1$, $R^2$ and Hal have the meanings given in the description, are used for controlling undesirable plant growth.

7 Claims, No Drawings

2H-1,2,4,6-THIATRIAZINE-1-DIOXIDES AND THEIR USE FOR CONTROLLING UNDESIRABLE PLANT GROWTH

The present invention relates to 2H-1,2,4,6-thiatriazine-1,1-dioxides, and to herbicides which contain these compounds as active ingredients.

It has been disclosed that substituted 6H-1,2,4,6-thiatriazin-5-one-1,1-dioxide derivatives are obtained when, for example, an adduct obtained from 2 moles of an isocyanate and one mole of chlorosulfonyl isocyanate is reacted with an alcohol (German Laid-Open Application DOS 1,946,262), or when an N'-carboalkoxy-N-sulfamylguanidine or -amidine is cyclized under alkaline conditions. These 6H-1,2,4,6-thiatriazin-5-one-1,1-dioxide derivatives exhibit herbicidal activity (German Laid-Open Applications DOS 2,508,832 and DOS 2,933,889).

We have found that 3-halo-2H-1,2,4,6-thiatriazine-1,1-dioxides of the formula

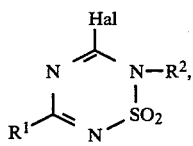

where $R^1$ is hydrogen, a saturated or unsaturated straight-chain aliphatic radical of not more than 10 carbon atoms, a saturated or unsaturated branched aliphatic radical of 3 to 10 carbon atoms, a straight-chain or branched saturated aliphatic radical of 2 to 10 carbon atoms which is substituted by halogen, alkoxy or alkylmercapto of 1 to 4 carbon atoms, a cycloaliphatic radical of 3 to 7 carbon atoms, alkylamino, alkenylamino, dialkylamino or dialkenylamino, where alkyl or alkenyl is of not more than 6 carbon atoms, phenyl which is unsubstituted or substituted by halogen, alkyl or alkoxy of 1 to 4 carbon atoms, or unsubstituted or halogen-substituted benzyl, $R^2$ is hydrogen, a straight-chain saturated or unsaturated aliphatic radical of not more than 10 carbon atoms, a branched saturated or unsaturated aliphatic radical of 3 to 10 carbon atoms, a cycloaliphatic radical of 3 to 7 carbon atoms, a haloalkyl radical of 2 to 10 carbon atoms or an alkoxyalkyl radical of 2 to 6 carbon atoms and Hal is halogen, have a selective herbicidal action and are useful intermediates for the preparation of dyes, drugs, and active ingredients for crop protection agents.

$R^1$ in formula I is hydrogen, a saturated or unsaturated straight-chain aliphatic radical of not more than 10, preferably not more than 4, carbon atoms, a saturated or unsaturated branched aliphatic radical of 3 to 10, preferably 3 to 4, carbon atoms, for example alkyl, alkenyl or alkynyl of not more than 10, preferably not more than 4, carbon atoms, such as methyl, ethyl, n-propyl, ispropyl, n-butyl, isobutyl, sec.-butyl, tert.-butyl, n-pentyl, n-hexyl, 1-ethyl-n-propyl, 1,2-dimethyl-n-propyl, 1,3-dimethyl-n-butyl, 1-ethyl-2-methyl-n-propyl, 1,2,2-trimethyl-n-propyl, 1,2-dimethyl-n-hexyl, tert.-amyl, allyl, methallyl, crotyl, 2-ethylhexen-2-yl, hexen-5-yl, 2-methylbuten-2-yl, 2-methyl-isobut-2-enyl, sec.-but-2-ynyl, butyn-2-yl, isobut-2-enyl, propargyl, 2-methylbut-3-enyl, 2-methyl-but-2-enyl or 1-methyl-isobut-2-enyl, a cycloaliphatic radical, for example cycloalkyl of 3 to 7 carbon atoms, such as cyclopropyl, cyclopentyl or cyclohexyl, alkylamino or dialkylamino where alkyl is of not more than 6 carbon atoms, eg. methylamino, dimethylamino, methylethylamino, diethylamino, allylamino or diallylamino, or hydrochlorides of these radicals, a straight-chain or branched saturated aliphatic radical of 2 to 10, preferably 2 to 4, carbon atoms which is substituted by halogen, alkoxy or alkylmercapto of 1 to 4 carbon atoms, for example haloalkyl, alkoxyalkyl or alkylmercaptoalkyl of 2 to 10, preferably 2 to 4, carbon atoms, such as 2-chloroethyl, 2-chloro-n-propyl, 3-chloro-n-propyl, 2-chloro-sec.-butyl, 2-chloro-isopropyl, 2-fluoro-sec.-butyl, 2-fluoro-isobutyl, 2-fluoro-isopropyl, 2-chloro-tert.-butyl, 2,2,2-trifluoroethyl, methoxyethyl, ethoxyethyl, 3-methoxy-n-propyl, methoxy-isopropyl, 3-methoxy-n-butyl, 1-methoxyethyl-n-propyl, methoxy-tert.-butyl, ethoxy-tert.-butyl, 2-methoxy-n-butyl, 4-methoxy-n-butyl, methylmercaptoethyl, ethylmercaptoethyl, 3-methylmercapto-n-propyl, 3-methylmercapto-n-butyl, 1-methylmercapto-but-2-yl, methylmercapto-tert.-butyl or 2-methylmercaptobutyl, phenyl which is unsubstituted or substituted by halogen, alkyl or alkoxy or 1 to 4 carbon atoms, eg. phenyl, 4-chlorophenyl, 3,4-dichlorophenyl, 4-tert.-butylphenyl, 4-methoxy-3-chlorophenyl, 4-methoxyphenyl, 2-methylphenyl or 2-methyl-4-chlorophenyl, or benzyl which is unsubstituted or substituted in the phenyl ring by halogen, such as fluorine, chlorine, bromine or iodine, eg. benzyl, 4-chlorobenzyl, 2,6-dichlorobenzyl, 2-chloro-6-fluorobenzyl or 2,6-difluorobenzyl.

$R^2$ in formula I is hydrogen, a saturated or unsaturated straight-chain aliphatic radical of not more than 10, preferably not more than 4, carbon atoms, a saturated or unsaturated branched aliphatic radical of 3 to 10, preferably 3 or 4, carbon atoms, for example alkyl, alkenyl or alkynyl of not more than 10, preferably not more than 4, carbon atoms, such as methyl, ethyl, n-propyl, isopropyl, n-butyl, isobutyl, sec-butyl, tert.-butyl, n-pentyl, n-hexyl, 1-ethyl-n-propyl, 1,2-dimethyl-n-propyl, 1,3-dimethyl-n-butyl, 1-ethyl-2-methyl-n-propyl, 1,2,2-trimethyl-n-propyl, 1,2-dimethyl-n-hexyl, tert.-amyl, allyl, methallyl,crotyl, 2-ethylhexen-2-yl, hexen-5-yl, 2-methylbuten-2-yl, 2-methyl-isobut-2-enyl, sec.-but-2-ynyl, butyn-2-yl, isobut-2-enyl, propargyl, 2-methylbut-3-enyl, 2-methylbut-2-enyl or 1-methyl-isobut-2-enyl, a cycloaliphatic radical of 3 to 7 carbon atoms, for example cycloalkyl of 3 to 7 carbon atoms, such as cyclopropyl, cyclopentyl or cyclohexyl, haloalkyl of 2 to 10, preferably 2 to 4, carbon atoms, eg. 2-chloroethyl, 2-chloro-n-propyl, 3-chloro-n-propyl, 2-chloro-sec.-butyl, 2-chloroisopropyl, 2-fluoro-sec.-butyl, 2-fluoroisobutyl, 2-fluoroisopropyl, 2-chloro-tert.-butyl or 2,2,2-trifluoroethyl, or alkoxyalkyl of 2 to 6, preferably 2 to 4, carbon atoms, eg. methoxyethyl, ethoxyethyl, 3-methoxy-n-propyl, methoxy-n-propyl, methoxyisopropyl, 3-methoxy-n-butyl, 1-methoxyethyl-n-propyl, methoxy-tert.-butyl, ethoxy-tert.-butyl, 2-methoxy-n-butyl or 4-methoxy-n-butyl.

Suitable halogens Hal in formula I are fluorine, chlorine, bromine and iodine.

Preferred compounds of the formula I are those in which $R^1$ and $R^2$ are each alkyl of 1 to 4 carbon atoms, in particular methyl or ethyl, and Hal is chlorine, or those in which $R^1$ is dialkylamino, where alkyl is of 1 to 3 carbon atoms, in particular dimethylamino, $R^2$ is hydrogen or alkyl of 1 to 4 carbon atoms, in particular methyl or ethyl, and Hal is chlorine.

The compounds of the formula I are obtained by reacting a compound of the formula

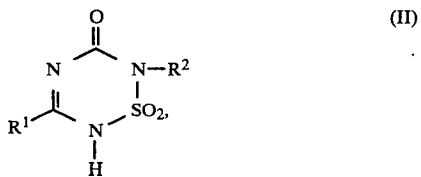

where $R^1$ and $R^2$ have the above meanings, or an alkali metal salt or alkaline earth metal salt thereof, with an acid halide of phosphoric acid, phosphorous acid, carbonic acid, oxalic acid or sulfurous acid, in the presence or absence of a solvent or diluent, and of a reaction accelerator.

If 2-ethyl-5-methyl-2H,1,2,4,6-thiatriazin-3-one-1,1-dioxide and phosphorus pentachloride are used as starting materials, the course of the reaction may be represented by the following equation:

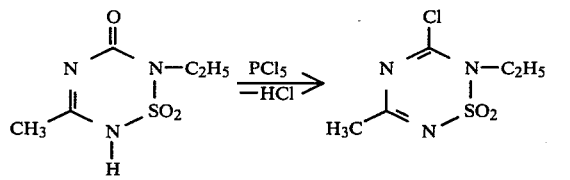

Advantageously, the reaction is carried out in a solvent or diluent which is inert under the reaction conditions. Examples of suitable solvents are halohydrocarbons, in particular chlorohydrocarbons, eg. tetrachloroethylene, 1,1,2,2- or 1,1,2,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, o-, m- and p-dichlorobenzene, o-, m- and p-dibromobenzene, o-, m- and p-chlorotoluene and 1,2,4-trichlorobenzene; ethers, eg. ethyl propyl ether, methyl tert.-butyl ether, di-n-butyl ether, diisopropyl ether, anisole, dioxane and ethylene glycol dimethyl ether; nitrohydrocarbons, eg. nitrobenzene, o-, m- and p-chloronitrobenzene and o-nitrotoluene; nitriles, eg. acetonitrile, butyronitrile, isobutyronitrile, benzonitrile and m-chlorobenzonitrile; aliphatic and cycloaliphatic hydrocarbons, eg. heptane, pinane, nonane, o-, m- and p-cymene, gasoline fractions boiling within a range of from 70° to 190° C., cyclohexane, methylcyclohexane, decalin, petroleum ether, hexane, naphtha, 2,2,4-trimethylpentane and 2,2,3-trimethylpentane; esters, eg. ethyl acetate; and appropriate mixtures of the above. Further suitable solvents are inorganic acid chlorides, eg. phosphorus oxychloride, and appropriate mixtures with inert chlorohydrocarbons, eg. 1,2-dichloroethane. Advantageously, the solvent is used in an amount of from 100 to 2,000, preferably from 200 to 700, % by weight, based on the starting material of the formula II.

Preferred acid halides are thionyl chloride, sulfur tetrafluoride, phosgene, oxalyl chloride and phosphorus tribromide, and in particular phosphorus pentachloride, phosphorus trichloride and phosphorus oxychloride. The reaction is carried out in general using an amount of from 1.0 to 1.5, preferably from 1.05 to 1.2, moles of acid halide per mole of the starting material II. Where a pentavalent halophosphorus compound is used, from 0.7 to 1.5, preferably from 1.0 to 1.2, moles of this are employed per mole of the starting material II.

Where a phosphorus(V) halide is used as the halogenating agent, it is advisable to employ a phosphorus oxyhalide as the diluent, advantageously in an amount of from 1 to 10 moles per mole of the starting material II.

The phosphorus(V) halide may also be prepared directly in situ, for example by reacting a mixture of a phosphorus(III) halide in the phosphorus oxyhalide, or in one of the above inert solvents, with the requisite stoichiometric amount of active halogen, for example by the method described in U.S. Pat. No. 1,906,440, after which the starting material II is added and the main reaction is effected.

Advantageous reaction accelerators to use are an N-disubstituted linear or cyclic carboxylic acid amide, a tetralkyl-substituted urea or a tertiary amine, in amounts of from 1 to 10% by weight, based on the starting material II. Mixtures of the said catalysts may also be used for the reaction. Furthermore, salts of amines, eg. the amine hydrochlorides, or quaternary salts of amines, may be used. Preferred catalysts are triethylamine, pyridine, N,N-dimethylaniline, N-ethylpiperidine, N-methylpyrrolidine, α, β- or γ-picoline, quinoline, isoquinoline, quinazoline, quinoxaline, n-propyldiisopropylamine, 2,6- and 2,4-lutidine, N-(pyrid-4-yl)-pyridinium chloride hydrochloride, p-dimethylaminopyridine, pyrimidine, acridine, dimethylformamide, diethylformamide, N-methyl-formanilide, N,N-dimethylacetamide, N-methylpyrrolidone and tetramethylurea.

Some of the 2H-1,2,4,6-thiatriazin-3-one-1,1-dioxides required as starting materials of the formula II are known; both these and the compounds not previously known can be prepared by reacting an N-carboalkoxyamidine with an aminosulfonyl halide. According to their spectroscopic data, the compounds have the structure shown in formula II. However, depending on the solvent used, a certain proportion of the tautomeric form

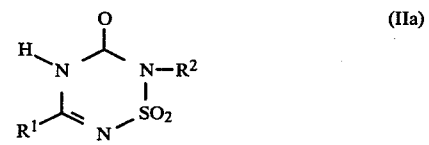

may also be present, and these compounds, being in equilibrium with the compounds II, also constitute preferred starting materials.

The process for the preparation of the compounds of the formula I is advantageously carried out by introducing the starting material II, with or without one of the above inert diluents, into the reaction vessel, adding the halogenating agent at from 0° to 60° C., preferably from 20° to 40° C., and then heating the mixture in accordance with the rate of evolution of gas.

However, it is also possible to add the starting material II, which may or may not be mixed with one of the above inert diluents, to the halogenating agent. Where phosgene is used, it is advisable to add a reaction accelerator, eg. dimethylformamide.

To complete the reaction, the mixture is then stirred for from 0.5 to 18 hours at from 0° to 160° C., preferably from 80° to 130° C. The degree of conversion can easily be followed by a spectroscopic method, for example by the shift in the proton resonance signals of the radicals $R^2$ or $R^1$.

The end product I is isolated from the reaction mixture in a conventional manner, for example by distilling off the solvent and the excess halogenating agent. This gives the desired end products in a pure form, though they may, if required, be purified by recrystallization, chromatography or distillation. When, in formula II, $R^1$ is a basic amino group, the end products, depending on the manner in which they are worked-up, are obtained as a rule in the form of their hydrochlorides, which may be washed in a basic medium to convert them to the free bases.

The methods given below relate to the preparation of the compounds of the formula I.

EXAMPLE 1

3-chloro-2,5-dimethyl-2H-1,2,4,6-thiatriazine-1,1-dioxide 212 parts of 2,5-dimethyl-2H-1,2,4,6-thiatriazin-3-one-1,1-dioxide were introduced into a stirred mixture of 292 parts of phosphorus pentachloride and 1,400 parts of phosphorus oxychloride at room temperature, and the mixture was heated to 110° C. in the course of 30 minutes. The reaction mixture was stirred under reflux for 6 hours and thereafter concentrated under reduced pressure, giving 234 parts (100% of theory) of 3-chloro-2,5-dimethyl-2H-1,2,4,6-thiatriazine-1,1-dioxide of: melting point 86°–90° C. (Compound No. 1) (NMR (60 MHz, CDCl$_3$): CH$_3$-C 2.4δ, CH$_3$-N 3.68δ).

EXAMPLE 2

3-chloro-2-ethyl-5-methyl-2H-1,2,4,6-thiatriazine-1,1-dioxide 225 parts of 2-ethyl-5-methyl-2H-1,2,4,6-thiatriazin-3-one-1,1-dioxide were added, in the course of 2 minutes, to a stirred mixture of 1,300 parts of phosphorus oxychloride and 292 parts of phosphorus pentachloride. The reaction mixture was stirred under reflux for 7 hours, and then concentrated under reduced pressure. The oil which remained was taken up in 350 parts of 1,2-dichloroethane, and the solution was chromatographed over neutral alumina (Activity I). After concentration, 230 parts (93% of theory) of 3-chloro-2-ethyl-5-methyl-2H-1,2,4,6-thiatriazine-1,1-dioxide of melting point 57°–59° C. were obtained (Compound No. 2) (NMR (60 MHz, CDCl$_3$): CH$_3$-C 2.3δ, N-CH$_2$ 3.68–4.03δ (q), CH$_3$-C 1.2–1.43δ (t)).

EXAMPLE 3

3-chloro-2-methyl-5-ethyl-2H-1,2,4,6-thiatriazine-1,1-dioxide 110 parts of phosphorus pentachloride were added to a stirred mixture of 86 parts of 2-methyl-5-ethyl-2H-1,2,4,6-thiatriazine-3-one-1,1-dioxide, 100 parts of 1,2-dichloroethane and 112 parts of phosphorus oxychloride at room temperature. The reaction mixture was then stirred under reflux for 12 hours. After concentration, 94 parts (100% of theory) of 3-chloro-2-methyl-5-ethyl-2H-1,2,4,6-thiatriazine-1,1-dioxide of $n_D^{25}=1.5331$ were obtained. (NMR (60 MHz, CDCl$_3$): CH$_3$-N 3.7δ). The very pure product ($n_D^{25}=1.5337$) boils at 123°–125° C./0.2 mbar (Compound No. 3).

EXAMPLE 4

3-chloro-2-methyl-5-dimethylamino-2H-1,2,4,6-thiatriazine-1,1-dioxide 34 parts of 2-methyl-5-dimethylamino-2H-1,2,4,6-thiatriazine-1,1-dioxide in 180 parts of 1,2-dichloroethane were saturated with hydrogen chloride gas, and the mixture was then concentrated under reduced pressure. The residue was suspended in 220 parts of phosphorus oxychloride, 34 parts of phosphorus pentachloride were added, and the reaction mixture was then stirred under reflux for 16 hours. After concentration under reduced pressure, 42 parts (97.5% of theory) of 3-chloro-2-methyl-5-dimethylamino-2H-1,2,4,6-thiatriazine-1,1-dioxide hydrochloride of melting point 119°–123° C. were obtained (Compound No. 4) (NMR (60 MHz, CDCl$_3$): CH$_3$-N 3.58δ).

The hydrochloride was taken up in 160 parts of methylene chloride, the solution was washed with dilute sodium carbonate solution, dried, and concentrated under reduced pressure, and 3-chloro-2-methyl-5-dimethylamino-2H-1,2,4,6-thiatriazine-1,1-dioxide of melting point 155°–157° C. were obtained (Compound No. 74).

The following compounds of the formula I

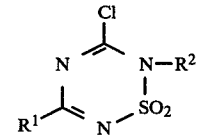

were obtained by a method similar to that described in Example 1:

| Compound Number | $R^1$ | $R^2$ | Physical data |
|---|---|---|---|
| 6 | CH$_3$ | i-C$_3$H$_7$ | bp. = 123–127° C./0.2 |
| 20 | C$_2$H$_5$ | CH$_2$—CH$_2$Cl | bp. = 133° C./0.2; $n_D^{25}$ = 1.5422 |
| 22 | n-C$_3$H$_7$ | CH$_3$ | $n_D^{25}$ = 1.5255 |
| 31 | i-C$_3$H$_7$ | CH$_3$ | bp. = 116° C./0.2; mp. = 62–67° C. |
| 33 | i-C$_3$H$_7$ | n-C$_3$H$_7$ | bp. = 123° C./0.2 |
| 44 | i-C$_4$H$_9$ | CH$_3$ | bp. = 119–120° C./0.2 |
| 68 | phenyl | CH$_3$ | bp. = 178–182° C./0.2 |
| 73 | (CH$_3$)$_2$N | CH$_3$ | mp. = 155–157° C. |
| 78 | CH$_3$ | n-C$_3$H$_7$ | bp. = 109° C./0.3 |

Examples of compounds of the formula I obtained by a method similar to that described in Example 1 are as follows:

| Compound no. | $R^1$ | $R^2$ | Physical data |
|---|---|---|---|
| 5 | H | CH$_3$ | |
| 7 | CH$_3$ | sec-C$_4$H$_9$ | |
| 8 | CH$_3$ | i-C$_4$H$_9$ | |
| 9 | CH$_3$ | tert.-C$_4$H$_9$ | |
| 10 | CH$_3$ | C$_6$H$_{11}$ | |
| 11 | CH$_3$ | CH$_2$—CH$_2$Cl | |
| 12 | CH$_3$ | CH$_2$—CH$_2$—O—CH$_3$ | |

-continued

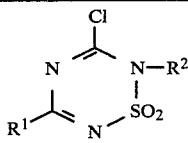

| Compound no. | $R^1$ | $R^2$ | Physical data |
|---|---|---|---|
| 13 | $C_2H_5$ | $C_2H_5$ | |
| 14 | $C_2H_5$ | $n$-$C_3H_7$ | |
| 15 | $C_2H_5$ | $i$-$C_3H_7$ | |
| 16 | $C_2H_5$ | $n$-$C_4H_9$ | |
| 17 | $C_2H_5$ | $i$-$C_4H_9$ | |
| 18 | $C_2H_5$ | sec-$C_4H_9$ | |
| 19 | $C_2H_5$ | tert.-$C_4H_9$ | |
| 21 | $C_2H_5$ | $C_6H_{11}$ | |
| 23 | $n$-$C_3H_7$ | $C_2H_5$ | |
| 24 | H | H | |
| 25 | $n$-$C_3H_7$ | $n$-$C_3H_7$ | |
| 26 | $n$-$C_3H_7$ | $i$-$C_3H_7$ | |
| 27 | $n$-$C_3H_7$ | sec-$C_4H_9$ | |
| 28 | $n$-$C_3H_7$ | tert.-$C_4H_9$ | |
| 29 | $n$-$C_3H_7$ | $CH_3$—O—$CH_2$—$CH_2$ | |
| 30 | $n$-$C_3H_7$ | $C_6H_{11}$ | |
| 32 | $i$-$C_3H_7$ | $C_2H_5$ | |
| 34 | $i$-$C_3H_7$ | $i$-$C_3H_7$ | |
| 35 | $i$-$C_3H_7$ | sec.-$C_4H_9$ | |
| 36 | $i$-$C_3H_7$ | $C_6H_{11}$ | |
| 37 | $n$-$C_4H_9$ | $CH_3$ | |
| 38 | $n$-$C_4H_9$ | $C_2H_5$ | |
| 39 | $n$-$C_4H_9$ | $n$-$C_3H_7$ | |
| 40 | $n$-$C_4H_9$ | $i$-$C_3H_7$ | |
| 41 | $n$-$C_4H_9$ | sec.-$C_4H_9$ | |
| 42 | $n$-$C_4H_9$ | $ClCH_2$—$CH_2$ | |
| 43 | $n$-$C_4H_9$ | $i$-$C_3H_7$ | |
| 45 | $i$-$C_4H_9$ | $i$-$C_3H_7$ | |
| 46 | sec.-$C_4H_9$ | $CH_3$ | |
| 47 | sec.-$C_4H_9$ | $C_2H_5$ | |
| 48 | sec.-$C_4H_9$ | $i$-$C_3H_7$ | |
| 49 | tert.-$C_4H_9$ | $CH_3$ | |
| 50 | tert.-$C_4H_9$ | $C_2H_5$ | |
| 51 | tert.-$C_4H_9$ | $i$-$C_3H_7$ | |
| 52 | $C_6H_{11}$ | $CH_3$ | |
| 53 | $C_6H_{11}$ | $C_2H_5$ | |
| 54 | $C_6H_{11}$ | $i$-$C_3H_7$ | |
| 55 | $CH_2$=CH—$CH_2$ | $CH_3$ | |
| 56 | $CH_2$=CH—$CH_2$ | $C_2H_5$ | |
| 57 | $CH_2$=CH—$CH_2$ | $i$-$C_3H_7$ | |
| 58 | benzyl | $CH_3$ | |
| 59 | benzyl | $i$-$C_3H_7$ | |
| 60 | 4-chlorobenzyl | $CH_3$ | |
| 61 | $CH_3$—O—$CH_2$—$CH_2$ | $CH_3$ | |
| 62 | $CH_3$—O—$CH_2$—$CH_2$ | $C_2H_5$ | |
| 63 | $CH_3$—S—$CH_2$—$CH_2$ | $CH_3$ | |
| 64 | $CH_3$—S—$CH_2$—$CH_2$ | $i$-$C_3H_7$ | |
| 65 | $CH_3$ | H | |
| 66 | $C_2H_5$ | H | |
| 67 | $CH_3$ | $CH_2$—CH=$CH_2$ | |
| 69 | benzyl | $CH_3$ | |
| 70 | phenyl | $i$-$C_3H_7$ | |
| 71 | 4-chlorobenzyl | $CH_3$ | |
| 72 | $(CH_3)_2N$ | H | |
| 74 | $(CH_3)(C_2H_5)N$ | $CH_3$ | |
| 75 | $(C_2H_5)_2N$ | $CH_3$ | |
| 76 | $(CH_2$=CH—$CH_2)_2N$ | $CH_3$ | |
| 77 | $(C_2H_5)_2N\cdot HCl$ | $CH_3$ | |

The compounds of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solids carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient. Examples of formulations are given below.

I. 90 parts by weight of the compound of Example 1 is mixed with 10 parts by weight of N-methyl-alpha-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of the compound of Example 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 20 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 6 is well mixed with 3 parts by weight of the sodium salt of diisobutyl-naphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 31 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or formulations containing them, may be applied pre- or postemergence. The agents may be applied before the unwanted plants have germinated from seed or sprouted from vegetative plant parts, or they may be applied to the leaves of unwanted and crop plants. Preferably, the novel active ingredients are applied during or after emergence of the unwanted plants, both on cropland and uncropped land. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year and the growth stage of the plants, and varies from 0.1 to 15 kg/ha and more, but is preferably from 0.5 to 4 kg/ha. The higher application rates are particularly suitable for total elimination of vegetation.

The herbicidal action of compounds of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated.

No cover was placed on the vessels in the postemergence treatment. The pots were set up in the greenhouse—species from warmer areas at from 20° to 30° C. and species from moderate climates at 15° to 25° C. The experiments were run for from 3 to 5 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The potted plants employed were *Chenopodium album, Datura stramonium, Galium aparine,* Matricaria spp., *Nicandra physoloides, Oryza sativa, Sinapis alba, Solanum nigrum, Zea mays,* and *Gossypium hirsutum.*

The results of these greenhouse experiments revealed that compound no. 1, applied preemergence at a rate of 2.0 kg/ha, had a good herbicidal action. Various crop plants remained substantially unaffected.

In view of the good tolerance of the active ingredients and the many application methods possible, the compounds according to the invention, or agents containing them, may be used in a large number of crop plants, apart from those used in the greenhouse experiments, for removing unwanted plant growth.

The following crop plants may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |

| Botanical name | Common name |
| --- | --- |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | parsley |
| Petroselinum crispum spp. tuberosum | |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel compounds according to the invention may be mixed and applied together with numerous representatives of other herbicidal or growth-regulating active ingredient groups. Examples of suitable mixture compnentes are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. To initiate the herbicidal action, wetting agents, spreader-stickers, and non-phytotoxic oils and oil concentrates may also be added.

We claim:

1. A 2H-1,2,4,6-thiatriazine-1,1-dioxide of the formula

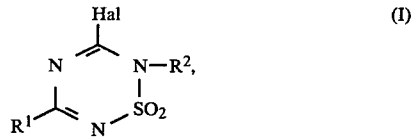

where $R^1$ is hydrogen, a saturated or unsaturated straight-chain aliphatic radical of not more than 10 carbon atoms, a saturated or unsaturated branched aliphatic radical of 3 to 10 carbon atoms, a straight-chain or branched saturated alipatic radical of 2 to 10 carbon atoms which is substituted by halogen, alkoxy or alkylmercapto of 1 to 4 carbon atoms, a cycloaliphatic radical of 3 to 7 carbon atoms, alkylamino, alkenylamino, dialkylamino or dialkenylamino, where alkyl or alkenyl is of not more than 6 carbon atoms, phenyl which is unsubstituted or substituted by halogen, alkyl or alkoxy of 1 to 4 carbon atoms, or unsubstituted or halogen-substituted benzyl, $R^2$ is hydrogen, a straight-chain saturated or unsaturated aliphatic radical of not more than 10 carbon atoms, a branched saturated or unsaturated aliphatic radical of 3 to 10 carbon atoms, a cycloaliphatic radical of 3 to 7 carbon atoms, a haloalkyl radical of 2 to 10 carbon atoms or an alkoxyalkyl radical of 2 to 6 carbon atoms and Hal is halogen.

2. A 2H-1,2,4,6-thiatriazine-1,1-dioxide of the formula I as claimed in claim 1, where $R^1$ and $R^2$ are alkyl of 1 to 4 carbon atoms or hydrogen, and Hal is chlorine.

3. A 2H-1,2,4,6-thiatriazine-1,1-dioxide of the formula I as claimed in claim 1, where $R^1$ is dialkylamino in which alkyl is of 1 to 3 carbon atoms, $R^2$ is hydrogen or alkyl of 1 to 4 carbon atoms and Hal is chlorine.

4. 3-Chloro-2,5-dimethyl-2H-1,2,4,6-thiatriazine-1,1-dioxide.

5. 3-Chloro-2-methyl-5-dimethylamino-2H-1,2,4,6-thiatriazine-1,1-dioxide.

6. A herbicide containing inert additives and, as active ingredient, a 2H-1,2,4,6-thiatriazine-1,1-dioxide of the formula I as claimed in claim 1.

7. A process for combating the growth of unwanted plants, wherein the plants and/or their location are treated with a herbicidally effective amount of a 2H-1,2,4,6-thiatriazine-1,1-dioxide of the formula I as claimed in claim 1.

* * * * *

UNITED STATES PATENT AND TRADEMARK OFFICE
CERTIFICATE OF CORRECTION

PATENT NO. : 4,426,219

DATED : January 17, 1984

INVENTOR(S) : Gerhard HAMPRECHT et al.

It is certified that error appears in the above-identified patent and that said Letters Patent is hereby corrected as shown below:

IN THE TITLE:

Correct the title to read:

2H-1,2,3,4,6-THIATRIAZINE-1,1-DIOXIDES AND THEIR USE FOR CONTROLLING UNDESIRABLE PLANT GROWTH

Signed and Sealed this

Fifteenth Day of May 1984

[SEAL]

Attest:

GERALD J. MOSSINGHOFF

Attesting Officer

Commissioner of Patents and Trademarks